US009250060B2

(12) United States Patent
Kang et al.

(10) Patent No.: US 9,250,060 B2
(45) Date of Patent: Feb. 2, 2016

(54) OPTICAL COHERENCE TOMOGRAPHY SYSTEM HAVING REAL-TIME ARTIFACT AND SATURATION CORRECTION

(75) Inventors: Jin Ung Kang, Ellicott City, MD (US); Yong Huang, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 13/586,586

(22) Filed: Aug. 15, 2012

(65) Prior Publication Data

US 2013/0044330 A1    Feb. 21, 2013

Related U.S. Application Data

(60) Provisional application No. 61/523,583, filed on Aug. 15, 2011.

(51) Int. Cl.
*A61B 5/00* (2006.01)
*G01B 9/02* (2006.01)
*G06T 5/00* (2006.01)

(52) U.S. Cl.
CPC ........ *G01B 9/02089* (2013.01); *G01B 9/02044* (2013.01); *G01B 9/02083* (2013.01); *G01B 9/02091* (2013.01); *A61B 5/0066* (2013.01); *G06T 5/002* (2013.01)

(58) Field of Classification Search
CPC .... A61B 5/0066; G06T 5/002; G06T 11/008; G06T 2207/10101
USPC .......................................... 382/128, 131, 275
See application file for complete search history.

(56) References Cited

U.S. PATENT DOCUMENTS

| 2009/0093980 A1* | 4/2009 | Kemp et al. ...................... 702/77 |
| 2009/0219379 A1* | 9/2009 | Rossato et al. .............. 348/14.01 |
| 2009/0306520 A1* | 12/2009 | Schmitt et al. ................ 600/476 |
| 2011/0157597 A1 | 6/2011 | Lu et al. |

OTHER PUBLICATIONS

Nvidia. N.p.: Nvidia, n.d. GeForce 9800 GT. Web. Feb. 5, 2014. <http://www.geforce.com/hardware/desktop-gpus/geforce-9800gt/specifications>.*
Nvidia. N.p.: Nvidia, n.d. GeForce GTX 480. Web. Feb. 5, 2014. <http://www.geforce.com/hardware/desktop-gpus/geforce-gtx-480/specifications>.*
Van der Jeught, Sam, Adrian Bradu, and Adrian Gh Podoleanu. "Real-time resampling in Fourier domain optical coherence tomography using a graphics processing unit." Journal of Biomedical Optics 15.3 (2010): 030511-030511.*

(Continued)

*Primary Examiner* — Chan Park
*Assistant Examiner* — Geoffrey E Summers
(74) *Attorney, Agent, or Firm* — Venable LLP; Henry J. Daley; F. Brock Riggs (57) ABSTRACT

An optical coherence tomography system having real-time artifact and saturation correction includes an optical coherence tomography unit, and a signal processing and display system adapted to communicate with the optical coherence tomography unit to receive imaging signals therefrom. The optical coherence tomography system is a Fourier Domain optical coherence tomography system. The signal processing and display system includes a parallel processor configured to correct the imaging signals, in real time, to at least partially remove image artifacts and saturation based on a subset of image data within an image frame.

8 Claims, 5 Drawing Sheets

(56) References Cited

OTHER PUBLICATIONS

Moon, Sucbei, Sang-Won Lee, and Zhongping Chen. "Reference spectrum extraction and fixed-pattern noise removal in optical coherence tomography." Optics express 18.24 (2010): 24395.*

Smith, Steven W. "The scientist and engineer's guide to digital signal processing." Chapter 15. (1997).*

Finch, Tony. "Incremental calculation of weighted mean and variance." University of Cambridge (2009).*

Gargesha, Madhusudhana, et al. "Denoising and 4D visualization of OCT images." Optics express 16.16 (2008): 12313-12333.*

"Interpolate". Oxford Dictionaries. Oxford University Press, n.d. Web. Aug. 6, 2014. <http://www.oxforddictionaries.com/us/definition/american_english/interpolate>.*

Li, Yan, Raj Shekhar, and David Huang. "Corneal pachymetry mapping with high-speed optical coherence tomography." Ophthalmology 113.5 (2006): 792-799.*

Moon, Sucbei, Sang-Won Lee, and Zhongping Chen. "Reference spectrum extraction and fixed-pattern noise removal in optical coherence tomography." Optics express 18.24 (2010): 24395-24404.*

Watanabe, Yuuki. "Real time processing of Fourier domain optical coherence tomography with fixed-pattern noise removal by partial median subtraction using a graphics processing unit." Journal of biomedical optics 17.5 (2012): 0505031-0505033.*

Zhang, Kang, and Jin U. Kang. "Graphics processing unit accelerated non-uniform fast Fourier transform for ultrahigh-speed, real-time Fourier-domain OCT." Optics express 18.22 (2010): 23472-23487.*

"Thread." Def. 1. Microsoft Computer Dictionary. 5th ed. Redmond: Microsoft, 2002. Safari Books Online. Web. Feb. 24, 2015.*

Asrani et al., "Detailed visualization of the anterior segment using Fourier-Domain optical coherence tomography," Arch Ophthalmol 126, 765-771 (2008).

Bezerra et al., "Intracoronary optical coherence tomography: a comprehensive review," JACC: Cardiovascular interventions 2, 1035-1046 (2009).

Boppart et al., "Intraoperative assessment of microsurgery with three-dimensional optical coherence tomography," *Radiology*, vol. 208, pp. 81-86, 1998.

Choma et al., "Swept source optical coherence tomography using an all-fiber 1300-nm ring laser source," Journal of Biomedical Optics 10(4), 044009 (2005).

Desjardins et al., "Real-time FPGA processing for high-speed optical frequency domain imaging," *IEEE Trans. Med. Imaging*, vol. 28, pp. 1468-1472, 2009.

Hofer et al., "Artefact reduction for cell migration visualization using spectral domain optical coherence tomography," J. Biophotonics 4, 355-367(2011).

Huang et al., "Optical coherence tomography," *Science*, vol. 254, pp. 1178-1181, 1991.

Huber et al., "Buffered Fourier domain mode locking: unidirectional swept laser sources for optical coherence tomography imaging at 370,000 lines/s," Opt. Lett., vol. 31, pp. 2975-2977, 2006.

Jeught et al., "Real-time resampling in Fourier domain optical coherence tomography using a graphics processing unit," J. Biomed. Opt., vol. 15, pp. 030511, 2010.

Klein et al., "Megahertz OCT for ultrawide-field retinal imaging with a 1050nm Fourier domain mode-locked laser," Opt. Express, vol. 19, pp. 3044-3062, 2011.

LaRocca et al., "Robust automatic segmentation of corneal layer boundaries in SDOCT images using graph theory and dynamic programming," Biomedical Optics Express 2(6), 1524-1538 (2011).

Leitgeb et al., "Complex and coherent noise free Fourier domain optical coherence tomography," in Optical Coherence Tomography, Technology and Applications, Drexler ed., 177-207 (Springer, 2008).

Li et al., "Performance and scalability of Fourier domain optical coherence tomography acceleration using graphics processing units," Appl. Opt., vol. 50, pp. 1832-1838, 2011.

Liu et al., "Real-time polarization-sensitive optical coherence tomography data processing with parallel computing," Appl. Opt., vol. 48, pp. 6365-6370, 2009.

Moon et al., Reference spectrum extraction and fixed-pattern noise removal in optical coherence tomography, Opt. Express 18, 24395-24404 (2010).

NVIDIA CUDA Zone: http://www.nvidia.com/object/cuda_home_new.html.

Oh et al., ">400 kHz repetition rate wavelength-swept laser and application to high-speed optical frequency domain imaging," Opt. Lett., vol. 35, pp. 2919-2921, 2010.

Potsaid et al., "Ultrahigh speed 1050nm swept source / Fourier domain OCT retinal and anterior segment imaging at 100,000 to 400,000 axial scans per second," Opt. Express, vol. 18, pp. 20029-20048, 2010.

Potsaid et al., "Ultrahigh speed Spectral / Fourier domain OCT ophthalmic imaging at 70,000 to 312,500 axial scans per second," Opt. Express, vol. 16, pp. 15149-15169, 2008.

Rasakanthan et al., "Processing and rendering of Fourier domain optical coherence tomography images at a line rate over 524 kHz using a graphics processing unit," J. Biomed. Opt., vol. 16, pp. 020505, 2011.

Ustun et al., "Real-time processing for Fourier domain optical coherence tomography using a field programmable gate array," Rev. Sci. Instrum., vol. 79, pp. 114301, 2008.

Watanabe et al., "Real-time display on Fourier domain optical coherence tomography system using a graphics processing unit," J. Biomed. Opt., vol. 14, pp. 060506, 2009.

Watanabe et al., "Real-time processing for full-range Fourier-domain optical-coherence tomography with zero-filling interpolation using multiple graphic processing units," Appl. Opt., vol. 49, pp. 4756-4762, 2010.

Wieser et al., "Multi-Megahertz OCT: High quality 3D imaging at 20 million A-scans and 4.5 GVoxels per second," Opt. Express, vol. 18, pp. 14685-14704, 2010.

Zhang et al., "Graphics processing unit accelerated non-uniform fast Fourier transform for ultrahigh-speed, real-time Fourier-domain OCT," Opt. Express, 18, pp. 23472-23487, 2010.

Zhang et al., "Real-time 4D signal processing and visualization using graphics processing unit on a regular nonlinear-k Fourier-domain OCT system," Opt. Express, vol. 18, pp. 11772-11784, 2010.

Zhang et al., "Real-time intraoperative 4D full-range FD-OCT based on the dual graphics processing units architecture for microsurgery guidance," Biomed. Opt. Express, vol. 2, pp. 764-770, 2011.

Zhang et al., "Real-time numerical dispersion compensation using graphics processing unit for Fourier-domain optical coherence tomography," Electronics Letters 47, 309-310 (2011).

* cited by examiner

OPTICAL COHERENCE TOMOGRAPHY SYSTEM HAVING REAL-TIME ARTIFACT AND SATURATION CORRECTION

CROSS-REFERENCE OF RELATED APPLICATION

This application claims priority to U.S. Provisional Application No. 61/523,583 filed Aug. 15, 2011, the entire content of which is hereby incorporated by reference.

This invention was made with Government support of Grant No. R21 1R21NS063131-01A1, awarded by the Department of Health and Human Services, The National Institutes of Health (NIH) and Grant No. IIP-0822695, awarded by the Department of Health and Human Services, The National Science Foundation (NSF). The U.S. Government has certain rights in this invention.

BACKGROUND

1. Field of Invention

The field of the currently claimed embodiments of this invention relates to optical coherence tomography systems, and more particularly to Fourier domain optical coherence tomography systems that have real-time artifact and saturation correction.

2. Discussion of Related Art

Optical coherence tomography (OCT) has been viewed as an "optical analogy" of ultrasound sonogram (US) imaging since its invention in early 1990's (D. Huang, E. A. Swanson, C. P. Lin, J. S. Schuman, W. G. Stinson, W. Chang, M. R. Hee, T. Flotte, K. Gregory, C. A. Puliafito, and J. G. Fujimoto, "Optical coherence tomography," Science, vol. 254, pp. 1178-1181, 1991). Compared to the conventional image-guided interventions (IGI) using modalities such as magnetic resonance imaging (MRI), X-ray computed tomography (CT) and ultrasound (US) (T. Peters and K. Cleary, *Image-Guided Interventions: Technology and Applications*, Springer, 2008), OCT has much higher spatial resolution and therefore possesses great potential for applications in a wide range of microsurgeries, such as vitreo-retinal surgery, neurological surgery and otolaryngologic surgery.

As early as the late 1990's, interventional OCT for surgical guidance using time domain OCT (TD-OCT) at a slow imaging speed of hundreds of A-scans/s has been demonstrated (S. A. Boppart, B. E. Bouma, C. Pitris, G. J. Tearney, J. F. Southern, M. E. Brezinski, J. G. Fujimoto, "Intraoperative assessment of microsurgery with three-dimensional optical coherence tomography," Radiology, vol. 208, pp. 81-86, 1998). Due to the technological breakthroughs in Fourier domain OCT (FD-OCT) during the last decade, ultrahigh-speed OCT is now available at >100,000 A-scan/s. For example, see the following:

B. Potsaid, I. Gorczynska, V. J. Srinivasan, Y. Chen, J. Jiang, A. Cable, and J. G. Fujimoto, "Ultrahigh speed Spectral/Fourier domain OCT ophthalmic imaging at 70,000 to 312,500 axial scans per second," Opt. Express, vol. 16, pp. 15149-15169, 2008.

R. Huber, D. C. Adler, and J. G. Fujimoto, "Buffered Fourier domain mode locking: unidirectional swept laser sources for optical coherence tomography imaging at 370,000 lines/s," Opt. Lett., vol. 31, pp. 2975-2977, 2006.

W-Y. Oh, B. J. Vakoc, M. Shishkov, G. J. Tearney, and B. E. Bouma, ">400 kHz repetition rate wavelength-swept laser and application to high-speed optical frequency domain imaging," Opt. Lett., vol. 35, pp. 2919-2921, 2010.

B. Potsaid, B. Baumann, D. Huang, S. Barry, A. E. Cable, J. S. Schuman, J. S. Duker, and J. G. Fujimoto, "Ultrahigh speed 1050 nm swept source/Fourier domain OCT retinal and anterior segment imaging at 100,000 to 400,000 axial scans per second," Opt. Express, vol. 18, pp. 20029-20048, 2010.

W. Wieser, B. R. Biedermann, T. Klein, C. M. Eigenwillig, and R. Huber, "Multi-Megahertz OCT: High quality 3D imaging at 20 million A-scans and 4.5 GVoxels per second," Opt. Express, vol. 18, pp. 14685-14704, 2010.

T. Klein, W. Wieser, C. M. Eigenwillig, B. R. Biedermann, and R. Huber, "Megahertz OCT for ultrawide-field retinal imaging with a 1050 nm Fourier domain mode-locked laser," Opt. Express, vol. 19, pp. 3044-3062, 2011.

For a spectrometer-based SD-OCT, an ultrahigh speed CMOS line scan camera based system has achieved up to 312,500 line/s in 2008 (Potsaid et al.); while for a swept laser type OCT, >20,000,000 line/s rate was achieved by multi-channel FD-OCT using a Fourier Domain Mode Locking (FDML) laser in 2010 (Wieser et al.).

Fourier-domain optical coherence tomography (FD-OCT) is a high-speed high-resolution three-dimensional imaging modality widely used in biomedical imaging. For OCT to find applications in the interventional imaging area, real-time image processing and display are required. The presence of the fixed-pattern-noise artifact that forms strong erroneous horizontal lines laying over the image is among the most common types of noise in FD-OCT systems (R. A. Leitgeb and M. Wojtkowski, "Complex and coherent noise free Fourier domain optical coherence tomography," in Optical Coherence Tomography, Technology and Applications, Wolfgang Drexler, and James G. Fujimoto, eds, 177-207 (Springer, 2008)). The fixed-pattern-noise artifact can be removed if the reference spectrum of that imaging frame is known. Therefore, in the case of high-resolution OCT imaging of a fixed site, simple subtraction of the reference spectrum from the OCT signal spectra works very effectively. However, the source spectrum shape varies over time; the OCT signal level and the spectra vary frame by frame; the optical phase and polarization can also vary frame to frame. Therefore, an effective signal processing method that can remove the DC levels due to these changes in real-time from the image data and thus remove the fixed pattern noise is of great importance in improving the quality of OCT images (Sucbei Moon, Sang-won Lee and Zhongping Chen, 'Reference spectrum extraction and fixed-pattern noise removal in optical coherence tomography', Opt. Express 18, 24395-24404 (2010); Bernd Hofer, Boris Považay, Boris Hermann, Sara M. Rey, Vedran Kajić, Alexandre Tumlinson, Kate Powell, Gerald Matz, and Wolfgang Drexler, "Artefact reduction for cell migration visualization using spectral domain optical coherence tomography," J. Biophotonics 4, 355-367 (2011)). However, periodically measuring and verifying the reference spectrum for OCT video imaging is highly inconvenient and impractical.

Saturation artifacts occur when light reflected back from a highly specular surface, generating signals that are over the dynamic range of the data acquisition system (Hiram G. Bezerra, Marco A. Costa, Giulio Guagliumi, Andrew M. Rollins and Daniel I. Simon, "Intracoronary optical coherence tomography: a comprehensive review," JACC: Cardiovascular interventions 2, 1035-1046 (2009)). It is not uncommon to see optical coherence tomography images that are corrupted by saturations artifacts, for example in cornea imaging (Sanjay Asrani, Marinko Sarunic, Cecilia Santiago, Joseph Izatt, "Detailed visualization of the anterior segment using Fourier-Domain optical coherence tomography," Arch Ophthalmol 126, 765-771 (2008); Francesco LaRocca, Stephanie J. Chiu, Ryan P. McNabb, Anthony, N. Kuo, Joseph A. Izatt, and Sina Farsiu, "Robust automatic segmentation of corneal layer boundaries in SDOCT images using graph theory and dynamic programming," Biomedical Optics Express 2(6), 1524-1538 (2011)), intracoronary imaging (Bezerra et al.), and finger pad imaging (Michael A. Choma, Kevin Hsu and Joseph A. Izatt, "Swept source optical coherence tomography using an all-fiber 1300-nm ring laser source," Journal of Biomedical Optics 10(4), 044009 (2005)). Real-time removal of the saturation artifacts can increase the diagnostic and interventional accuracy. There thus remains a need for improved Fourier domain optical coherence tomography systems that have real-time artifact and saturation correction.

SUMMARY

An optical coherence tomography system having real-time artifact and saturation correction according to some embodiments of the current invention includes an optical coherence tomography unit, and a signal processing and display system adapted to communicate with the optical coherence tomography unit to receive imaging signals therefrom. The optical coherence tomography system is a Fourier Domain optical coherence tomography system. The signal processing and display system includes a parallel processor configured to correct the imaging signals, in real time, to at least partially remove image artifacts and saturation based on a subset of image data within an image frame.

An optical coherence tomography method according to some embodiments of the current invention includes receiving imaging signals from a Fourier Domain optical coherence tomography unit, correcting the imaging signals, in real time, using a parallel processor to at least partially remove image artifacts and saturation based on a subset of image data within an image frame, and displaying a multiframe video image after the correcting in real time.

A computer readable medium according to some embodiments of the current invention includes software, which software when executed by a computer that has a parallel processor causes the computer to receive imaging signals from a Fourier Domain optical coherence tomography unit, correct the imaging signals, in real time, using the parallel processor to at least partially remove image artifacts and saturation based on a subset of image data within an image frame, and display a multiframe video image after the correcting in real time.

BRIEF DESCRIPTION OF THE DRAWINGS

Further objectives and advantages will become apparent from a consideration of the description, drawings, and examples.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

The term "light" as used herein is intended to have a broad meaning that can include both visible and non-visible regions of the electromagnetic spectrum. For example, visible, near infrared, infrared and ultraviolet light are all considered as being within the broad definition of the term "light."

The term "real-time" is intended to mean that the OCT images, with corrections for artifacts and saturation, can be provided to the user during use of the OCT system. In other words, any noticeable time delay between detection and image displaying to a user is sufficiently short for the particular application at hand. In some cases, the time delay can be so short as to be unnoticeable by a user.

The term "image artifact" refers to patterns in an image that do not correspond to the object being imaged and which are non-transient on time scales that are long compared to random noise events. For example, image artifacts can include fixed-pattern-noise artifacts.

Since A-scan OCT signals are acquired and processed independently, the reconstruction of an FD-OCT image is inherently ideal for parallel processing methods, such as multi-core CPU parallelization (G. Liu, J. Zhang, L. Yu, T. Xie, and Z. Chen, "Real-time polarization-sensitive optical coherence tomography data processing with parallel computing," *Appl. Opt.*, vol. 48, pp. 6365-6370, 2009) and FPGA hardware acceleration (T. E. Ustun, N. V. Iftimia, R. D. Ferguson, and D. X. Hammer, "Real-time processing for Fourier domain optical coherence tomography using a field programmable gate array," *Rev. Sci. Instrum.*, vol. 79, pp. 114301, 2008; A. E. Desjardins, B. J. Vakoc, M. J. Suter, S. H. Yun, G. J. Tearney, B. E. Bouma, "Real-time FPGA processing for high-speed optical frequency domain imaging," *IEEE Trans. Med. Imaging*, vol. 28, pp. 1468-1472, 2009). Recently, cutting-edge general purpose computing on graphics processing units (GPGPU) technology has been gradually utilized for ultra-high speed FD-OCT imaging. See, for example:

- Y. Watanabe and T. Itagaki, "Real-time display on Fourier domain optical coherence tomography system using a graphics processing unit," J. Biomed. Opt., vol. 14, pp. 060506, 2009.
- K. Zhang and J. U. Kang, "Real-time 4D signal processing and visualization using graphics processing unit on a regular nonlinear-k Fourier-domain OCT system," Opt. Express, vol. 18, pp. 11772-11784, 2010.
- S. V. Jeught, A. Bradu, and A. G. Podoleanu, "Real-time resampling in Fourier domain optical coherence tomography using a graphics processing unit," J. Biomed. Opt., vol. 15, pp. 030511, 2010.
- Y. Watanabe, S. Maeno, K. Aoshima, H. Hasegawa, and H. Koseki, "Real-time processing for full-range Fourier-domain optical-coherence tomography with zero-filling interpolation using multiple graphic processing units," Appl. Opt., vol. 49, pp. 4756-4762, 2010.
- K. Zhang and J. U. Kang, "Graphics processing unit accelerated non-uniform fast Fourier transform for ultrahigh-speed, real-time Fourier-domain OCT," Opt. Express, 18, pp. 23472-23487, 2010.
- K. Zhang and J. U. Kang, "Real-time intraoperative 4D full-range FD-OCT based on the dual graphics processing units architecture for microsurgery guidance," Biomed. Opt. Express, vol. 2, pp. 764-770, 2011.
- J. Rasakanthan, K. Sugden, and P. H. Tomlins, "Processing and rendering of Fourier domain optical coherence tomography images at a line rate over 524 kHz using a graphics processing unit," J. Biomed. Opt., vol. 16, pp. 020505, 2011.
- J. Li, P. Bloch, J. Xu, M. V. Sarunic, and L. Shannon, "Performance and scalability of Fourier domain optical coherence tomography acceleration using graphics processing units," Appl. Opt., vol. 50, pp. 1832-1838, 2011.
- K. Zhang, and J. U. Kang, "Real-time numerical dispersion compensation using graphics processing unit for Fourier-domain optical coherence tomography," Elect. Lett., vol. 47, pp. 309-310, 2011.

Compared to FPGAs and multi-core processing methods, GPGPU acceleration is more cost-effective in terms of price/performance ratio and convenience of system integration: one or multiple GPUs can be directly integrated into the FD-OCT system in the popular form of a graphics card without requiring any optical modifications. Moreover, as with its original purpose, GPUs are also highly suitable for implementing volume rendering algorithms on reconstructed 3D data sets, which provides a convenient unified solution for both reconstruction and visualization.

According to some embodiments of the current invention, we developed an optimized algorithm for GPUs based on the minimum variance mean-line subtraction (MVMS) method which was first proposed by Moon et al to remove the reference fixed pattern artifact. To improve upon and to address a commonly encountered problem with a large fluctuation of the signal intensity, we developed and incorporated an algorithm to also perform automatic detection of the saturated scan lines and correction using linear interpolation of adjacent normal A-scan lines. We optimized both methods for the GPU architecture and successfully integrated them with existing GPU-based OCT signal processing to demonstrate real-time fixed-pattern-noise-free and automatic saturation artifact correction FD-OCT video imaging at 70 frames/s for a frame size of 1000 (lateral)×1024 (axial) pixels in one example according to an embodiment of the current invention. The theoretical maximum processing and rendering rate was calculated to be 266,000 A-scans/s.

Figure 1:
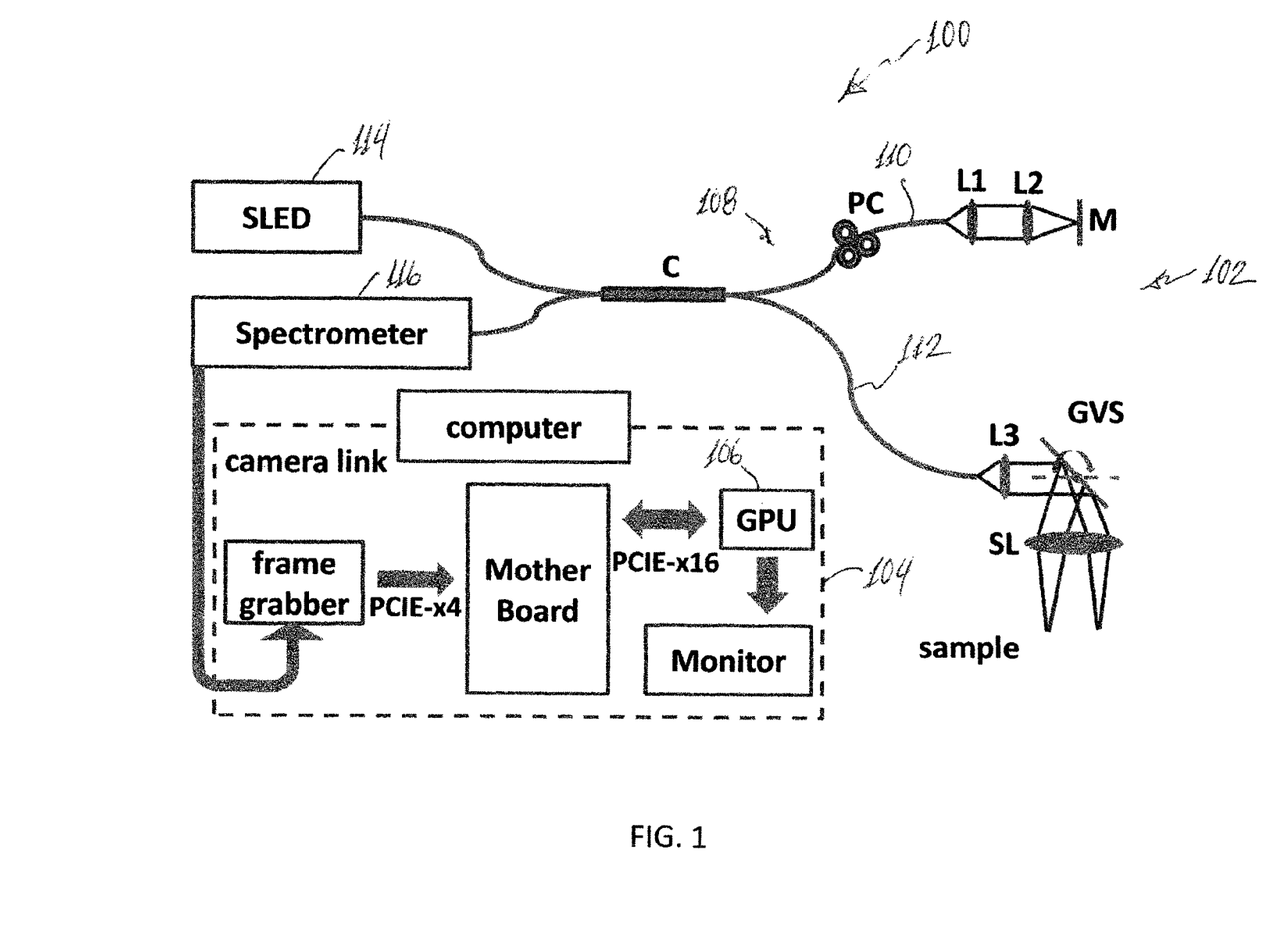
FIG. 1 is a schematic illustration of an optical coherence tomography system having real-time artifact and saturation correction according to an embodiment of the current invention. The system configuration includes C: 50-50 broadband fiber coupler; L1, L2, L3: achromatic lenses; M: mirror; GVS: galvanometer pairs; PC: polarization controller; SL: scanning lens.

FIG. 1 provides a schematic illustration of an optical coherence tomography (OCT) system 100 according to an embodiment of the current invention that has real-time artifact and saturation correction. The OCT system 100 includes an optical coherence tomography unit 102 and a signal processing and display system 104 adapted to communicate with the optical coherence tomography unit 102 to receive imaging signals therefrom. The OCT system 100 is a Fourier Domain OCT system. The signal processing and display system 104 includes a parallel processor 106 configured to correct the imaging signals, in real time, to at least partially remove image artifacts and saturation based on a subset of image data within an image frame.

The OCT system 100 includes a fiber-optic system 108 that includes a reference path 110 and an observation path 112, a light source 114 optically coupled to the fiber-optic system 108 to illuminate the reference and observation paths (110, 112), and an optical detection system 116 arranged to receive combined light returned along the reference and observation paths (110, 112). The optical detection system 116 provides the imaging signals.

The parallel processor 106 can be one or more graphics processing units (GPUs) according to an embodiment of the current invention. The optical detection system 116 can include a spectrometer according to an embodiment of the current invention to detect spectral components of light returned from the target.

In an embodiment, the parallel processor 106 can be configured to detect saturation in an A-line of an image frame and to correct the A-line based on a non-saturated A-line within the image frame. The non-saturated A-line within the image frame can be a nearest non-saturated A-line to the saturated A-line within the image frame in an embodiment.

In an embodiment, the parallel processor 106 can be configured to correct the imaging signals based on a minimum variance mean-line subtraction (MVMS) method to remove the image artifacts. In some embodiments, the minimum variance mean-line subtraction (MVMS) method can be implemented based on a recursion relation. An embodiment of a recursion relation will be described in more detail below along with some examples.

In some embodiments, the optical coherence tomography system 100 can be configured to provide at least ten (10) image frames per second in which each image frame has a size that is at least 512×512 and each image frame is corrected in real time to remove image artifacts and saturation based on a subset of image data within each respective image frame.

In some embodiments, the optical coherence tomography system 100 can be configured to provide at least seventy (70) image frames per second in which each image frame has a size that is at least $1000 \times 10^{24}$ and each image frame is corrected in real time to remove image artifacts and saturation based on a subset of image data within each respective image frame.

In some embodiments, the optical coherence tomography system 100 can be based on other types of Fourier domain OCT such as swept-source OCT.

Figure 2:
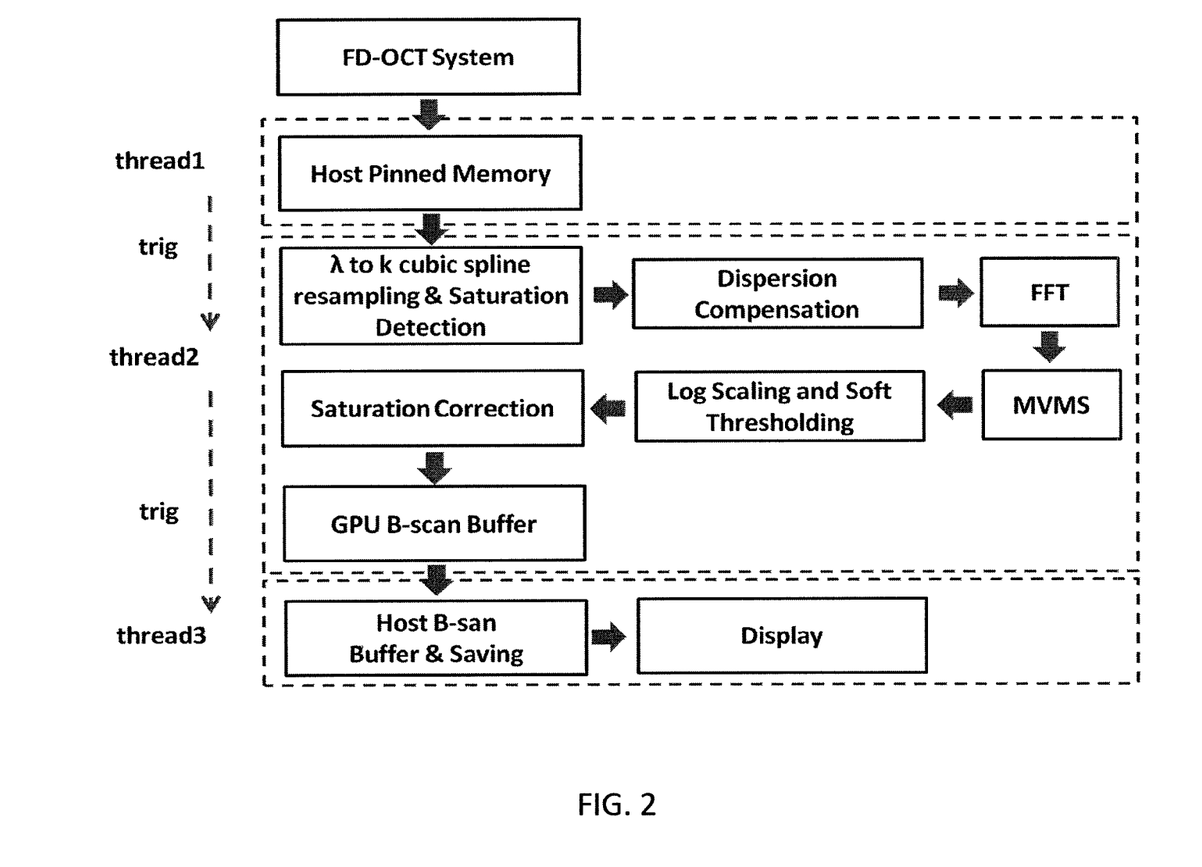
FIG. 2 is a flowchart illustrating a data processing architecture according to an embodiment of the current invention. Dashed arrows: thread triggering; solid arrows: data stream. Here the entire GPU memory buffers were allocated on the global memory. Thread 1 controls the data acquisition, thread 2 controls the data processing that is all done on GPU, and thread 3 controls the image display. Dashed squares indicate the task of each thread.

FIG. 2 is a flowchart illustrating a data processing architecture that can be implemented on the parallel processor 106 according to an embodiment of the current invention. In an embodiment, the parallel processor 106 can be configured to perform other image processing functions in addition to saturation detection and correction and artifact removal. For example, any combination of the previously mentioned image processing functions can be included in combination, some of which are illustrated schematically in FIG. 2. For example, the GPU can be configured to also perform dispersion compensation. The GPU can also be configured to perform a Fast Fourier Transform (FFT) on the dispersion-compensated spectrum. However, the general concepts of the current invention are not limited to these examples.

Further additional concepts and embodiments of the current invention will be described by way of the following examples. However, the broad concepts of the current invention are not limited to these particular examples.

EXAMPLES

Some examples according to an embodiment of the current invention was demonstrated using an in-house developed spectral-domain OCT. The system configuration is shown schematically in FIG. 1. The customized spectrometer was built using a 12-bit, 70 kHz, 2048 pixel, CCD line-scan (EM4, e2v, USA) as the detector. A superluminescent (SLED) light source with an output power of 10 mW and an effective bandwidth of 105 nm centered at 845 nm, which gave the theoretical axial resolution of 3.0 μm in air, was used for the demonstrations. A quad-core @ 2.4 GHz Dell Precision T7500 workstation was used to host a frame grabber (NI PCIe-1429, PCIE-x4 interface) and an NVIDIA GeForce GTX 590 GPU (PCIE-x16 interface, 32 stream multiprocessors, 1024 cores at 1.21 GHz, 3 GB graphics memory). Residual dispersion of the system caused by the components, L1, L2, L3, SL, and the optical fibers was compensated numerically through a GPU process described in (Kang Zhang and Jin U. Kang, "Real-time numerical dispersion compensation using graphics processing unit for Fourier-domain optical coherence tomography," Electronics Letters 47, 309-310 (2011)). All the data acquisition, image processing, and rendering were performed on this multi-thread, CPU-GPU heterogeneous computing system. A customized user interface was designed and programmed through C++ (Microsoft Visual Studio, 2008). CUDA (Computer Unified Device Architecture) 4.0 from NVIDIA (Santa Clara, Calif.) was used to program the GPU for the general purpose computation (NVIDIA CUDA Zone: http://www.nvidia.com/object/cuda_home_new.html).

FIG. 2 shows the data processing flowchart of the OCT system. The acquired data (16-bit unsigned integer format) from the frame grabber was stored in a host pinned or page-locked memory buffer before the GPU processing. This eliminated the need for having to copy the data to the GPU global memory in mapped memory method supported by CUDA 4.0. The GPU processing included cubic resampling, saturation detection, dispersion compensation, FFT, MVMS, log scaling, soft thresholding and saturation correction if necessary to form the final OCT image data. The image data were then copied back to the host memory for the display and for saving. Details of the implementation of the signal processing other than MVMS, saturation detection and correction can be found in above-noted references.

In the MVMS scheme, a segment of the minimum variance is selected for its mean value $\mu_\Omega(z)$ to be assigned as the A-line value of that axial position, z.

$$\mu_\Omega(z) = \frac{1}{L}\sum_{l\in\Omega} g_l(z) \qquad (1)$$

where $\Omega$ represents a segment of the A-line data, and L is the number of data points of $\Omega$. $g_l(z)$ is a complex A-line data point obtained after Fourier transform of the cubic spline interpolated spectrum. The segmental variance, $v_\Omega$ is defined as $$v_\Omega = \frac{1}{L}\sum_{l\in\Omega}(\text{Re}\{g_l\} - \text{Re}\{\mu_\Omega\})^2 + \frac{1}{L}\sum_{l\in\Omega}(\text{Im}\{g_l\} - \text{Im}\{\mu_\Omega\})^2. \qquad (2)$$

The mean of the segment, whose variance is the minimum in a horizontal line, is assigned to the reference A-line for an axial position of z (Sucbei Moon, Sang-won Lee and Zhongping Chen, 'Reference spectrum extraction and fixed-pattern noise removal in optical coherence tomography', Opt. Express 18, 24395-24404 (2010)).

To implement this method in real-time on a GPU architecture, a customized data structure composed by three floating point numbers (the mean value of the real part, the mean value of the imaginary part, and the variance) were used. The reference A-line is represented by the data structure unit with a length of half the number of data points in one A-scan spectrum. After a reference A-line was obtained, it was subtracted from the image in the later log scaling and soft thresholding step. To make formula (1), (2) more suitable for the GPU thread execution, a recursion method was used to minimize the thread global memory read operation, as is shown in (3), (4), as follows:

$$\mu_{l+1}(z) = \mu_l(z) + \frac{1}{l+1}(g_l(z) - \mu_l(z)) \qquad (3)$$

$$v(z)_{l+1}^2 = v(z)_l^2 + \frac{1}{l+1}\left[\frac{l}{l+1}(g_{l+1}(z) - \mu_l(z))^2 - v(z)_l^2\right] \qquad (4)$$

Increasing index l one by one will lead to a final variance and mean value of that segmentation. The recursion method decreases the memory read operation by half. The algorithm was further optimized through block and grid design of the GPU kernel launch and the optimization of the segmentation numbers for certain lateral A-scan numbers in each frame. For a frame with 1000 lateral pixel size, a block size of 128 threads and a grid size of 128 were found to be optimal. This way each stream multiprocessor has 8 blocks running simultaneously. The segmentation number of 10 was found to be optimum according to some embodiments, and the result was based on previous kernel function launch configuration of 5, 10, 20 segmentations.

The saturation detection process was combined with the cubic spline interpolation to make the signal processing seamless. Since the spectrometer's dynamic range is 12-bit, the outputs are expressed in values between 0 to 4095. Therefore an unsaturated spectrum should have all values less than 4095. While each A-line spectrum point are being calculated, the number of points within that A-scan that have values equal to 4095 are updated. If the number of points in that A-scan contains more than two points that are saturated, that A-line spectrum is marked as a saturated A-line. This is done by changing the corresponding status flag to false in an array that records the status of each A-line. The saturation correction was performed in the spatial image domain after log resealing and soft thresholding. The kernel function checks the status of each A-line of the processed frame. If a certain A-line is marked as false, then the program searches the most adjacent upper and bottom A-lines that are marked as true. Then that A-line was corrected by linear interpolation of the upper and bottom A-lines.

Results and Discussion

CUDA profiler 4.0 from CUDA Toolkit 4.0 (NVIDIA CUDA Zone: http://www.nvidia.com/object/cuda_home_new.html) was used to analyze the time cost of each kernel function of our GPU program according to an embodiment of the current invention. We launched five sessions of our application, each session ran the application five times. All of the following time costs are based on the average measured value with standard deviation marked.

The GPU processing time for MVMS based on (1), (2) was 440±0.6 μs and (3), (4) was 400±0.6 μs for image frame size of 1024×1000. This simple comparison shows that the proposed recursive MVMS processing method improves the processing speed as we expected, though it is only a 10% time cost reduction. To verify the speedup compared to a CPU-based recursion method, the same MVMS processing method based on (3), (4) was implemented on the same workstation where the GPU was hosted using C++(Microsoft Visual Studio, 2008) and the CPU was the only computing source. The artificial generated frame of complex data was 1024×1000 in size. The CPU-based MVMS was performed with 10 segmentations with 100 points within each. Running the same procedure 1000 times, the averaged time cost was measured to be 55.22±0.54 ms. This shows that the GPU-based MVMS method according to an embodiment of the current invention provided 138 times the speed enhancement compared to a CPU-based MVMS method.

The saturation detection step added very little computation burden to the cubic spline interpolation processing. We measured the time cost of the cubic spline interpolation and cubic spline interpolation combining saturation detection. The additional time cost for the saturation detection was 90±0.15 μs. The saturation correction step costs 36±0.07 μs. Note that this time cost may vary depending on how many saturated A-lines there are within one frame. The total time cost for the saturation corrected imaging is only 126±0.22 μs.

Figure 3:
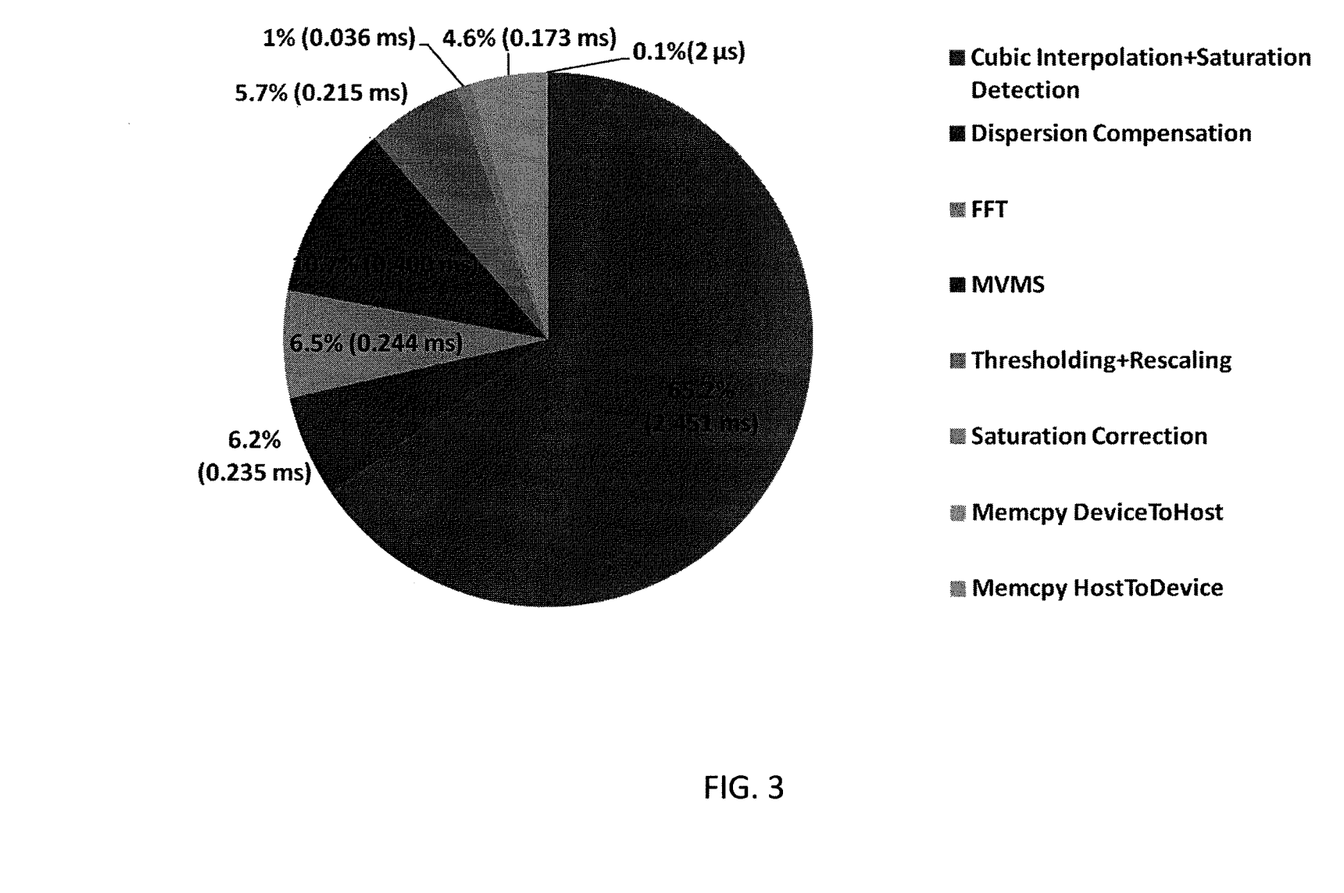
FIG. 3 is a pie chart of time cost of all system GPU kernel functions.

The time cost for all the system GPU kernel functions for a single image frame size of 1024×1000, corresponding to spectrum data size of 2048×1000, is presented in the pie chart in FIG. 3. As can be seen from FIG. 3, cubic interpolation of the spectrum data was the main GPU computational consumer. Optimization of the cubic interpolation was obtained (Kang Zhang and Jin U. Kang, "Real-time numerical dispersion compensation using graphics processing unit for Fourier-domain optical coherence tomography," Electronics Letters 47, 309-310 (2011)). By using the pinned memory, the explicit data transfer from host to GPU is negligible. Note that different implementation and optimization might cause various cost time distribution. For our system in this case, MVMS takes 10.5% of the total GPU computing time, saturation detection and correction takes 2.4% and 1% respectively. The total GPU time is 3.76±0.01 ms, which corresponds to the maximum imaging speed of 266,000 A-lines/s, which is well above the camera imaging speed of 70,000 A-lines/s and provides enough room for further GPU accelerated functionality. In further embodiments, our software processing system could benefit significantly from a wavelength swept-source OCT operating with a k-clock and other Fourier Domain OCT systems that are based on k-sampled spectrometer. If cubic interpolation can be saved, the system could potentially run at peak processing speed of 714,000 A-lines/s.

Figures 4A, 4B, 4C, 4D, 4E, 4F, 4G, 4H, 4I, 4J, 4K:
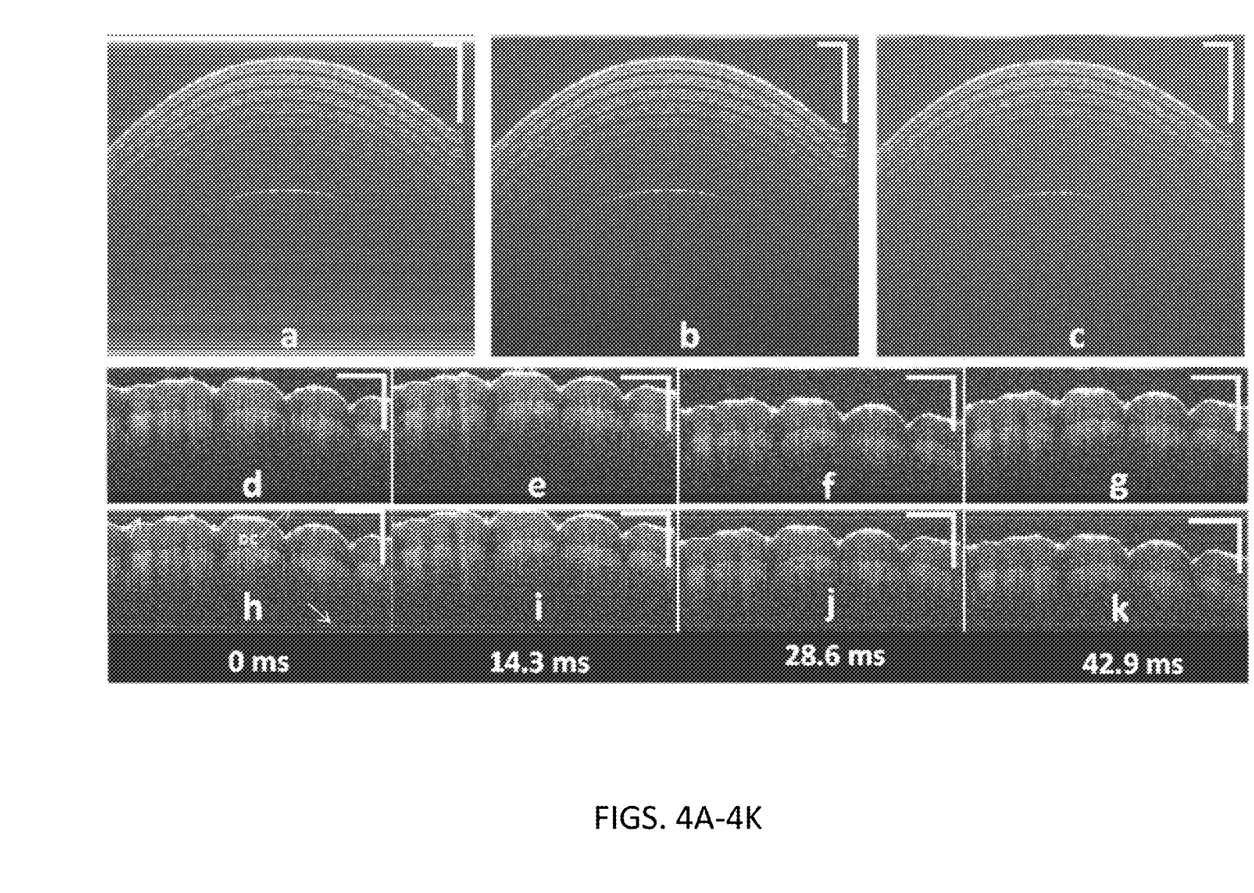
FIGS. 4A-4K show examples of images of a layered polymer phantom: a, without reference subtraction (FIG. 4A); b, real time reference A-line subtraction (FIG. 4B); c, physical reference spectrum subtraction, and real-time in vivo fingertip video imaging (d)-(g) with reference correction (FIGS. 4D-4G) and (h)-(k) without reference correction (FIGS. 4H-4K). (The time bar was marked on the bottom, scale bar is 400 μm, white arrows indicate several obvious fixed pattern noise.)

To demonstrate the effectiveness of the MVMS method, we imaged a layered polymer phantom and a human finger and analyzed the result. The result is shown in FIGS. 4A-4K. FIG. 4A is an image without the reference subtraction. One can clearly see the strong horizontal line artifacts running across the image. FIG. 4B is an image using MVMS processing; FIG. 4C is an image obtained with the physical reference subtraction. The physical reference was measured before the image acquisition by blocking the sample arm and was subtracted from the measured spectrum during the image acquisition process. We can clearly see that MVMS processing removes the fixed pattern artifact cleanly and performs better than physical reference subtraction in terms of image visibility. Further analysis of the images shows that the image in FIG. 4B exhibits 2 dB SNR improvements over the image in FIG. 4C. The reason for this improvement is that MVMS performed in real-time is more effective in removing the effect of variation of reference spectrum and other DC component variations during the image acquisition process. As wavelength dependent absorption and scattering coming from the imaging sample will change the reflected spectrum, the physical reference spectrum measured when there is no sample at the sample arm doesn't truly reflect the effective reference spectrum that should be subtracted. We also obtained video sequences of an in vivo human fingertip captured at 70 Hz with and without MVMS processing; and they are shown in FIGS. 4D-4G and FIGS. 4H-4K, respectively. One can clearly see that fixed-pattern-artifact was effectively removed in FIG. 4H-4H.

Figures 5A, 5B:
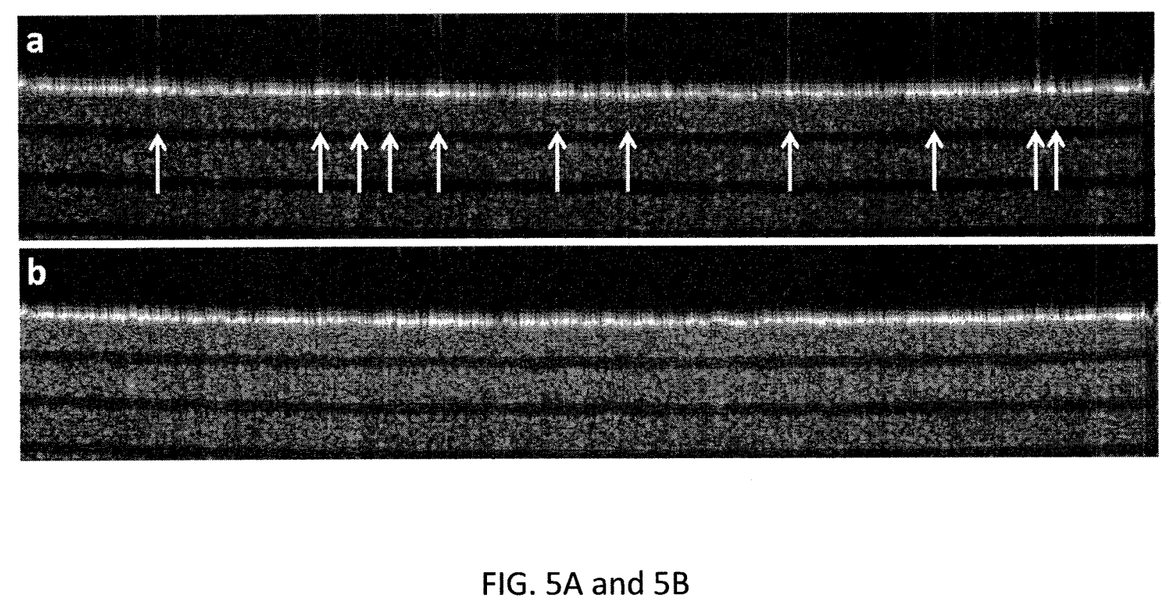
FIGS. 5A and 5B show an example of a layered polymer phantom imaging (a) (FIG. 5A) without saturation detection and correction (b) (FIG. 5B) with saturation detection and correction. (The saturated lines are identified by arrows.)

To further demonstrate the effectiveness of the saturation detection and correction, we imaged a layered polymer phantom again. The layer polymer phantom was chosen due to its abundance of highly specular reflections along the scanning surface. We also increased the integration time of our system to make the saturation occur more frequently. The result is shown in FIGS. 5A and 5B. The images are cropped to the first 100 pixels in the axial direction to clearly show the saturation artifacts. We scanned the same area of interest with and without the saturation detection and correction. FIG. 5A is the saved image frame without the saturation detection and correction. The saturation areas are marked with arrows on the image. FIG. 5B is the same image with the saturation detection and correction. We can see clearly that the saturation artifacts have been detected and removed. Here the saturation correction was performed with a linear interpolation. Switching to cubic interpolation can increase the interpolation accuracy but with more time cost. When there are large areas of continuous saturation, the interpolation would cause errors. In that case, the system integration time and reference level needs to be adjusted dynamically instead.

CONCLUSION

In conclusion, we implemented a real-time reference A-line subtraction, and saturation detection and correction technique for high-frame rate FD-OCT video imaging on a GPU architecture to remove the fixed pattern noise and saturated artifacts in some examples according to an embodiment of the current invention. This method according to some embodiments of the current invention has been shown to be highly effective in removing the fixed pattern noise and saturated artifacts and can be easily integrated into GPU-based, real-time FD-OCT signal processing. Our system in this example was configured to operate at 70 fps with a frame size of 1024×1000 and significantly improved the quality of the OCT video. The system is capable of operating up to 266,000 A-lines/s. The system can be applied for interventional imaging of microsurgical procedures, for example.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. An optical coherence tomography system having real-time artifact and saturation correction, comprising:
an optical coherence tomography unit; and
a signal processing and display system adapted to communicate with said optical coherence tomography unit to receive imaging signals therefrom,
wherein said optical coherence tomography system is a Fourier Domain optical coherence tomography system,
wherein said signal processing and display system comprises a parallel processor configured for multithreaded operation comprising a first thread for data acquisition of said imaging signals from said optical coherence tomography unit, a second thread for data processing of said imaging signals, and a third thread for image display of image frames generated from said second thread,
wherein said first, second, and third threads are synchronized such that said second thread is triggered by said first thread, and said third thread is triggered by said second thread,
wherein said second thread of said parallel processor is configured to correct said imaging signals, in real time, to at least partially remove image artifacts and saturation based on a subset of image data within an image frame,
wherein, to correct said imaging signals, said parallel processor is configured to subtract a reference A-line from said imaging signals, said reference A-line being represented by a data structure unit of three floating point numbers including a mean value of a real part of said imaging signals, a mean value of an imaginary part of said imaging signals, and a variance of said imaging signals,
wherein said second thread of said parallel processor is configured to detect saturation in an A-line of said image frame and to correct said A-line based on a non-saturated A-line within said image frame, said non-saturated A-line within said image frame being a nearest non-saturated A-line to said saturated A-line within said image frame,
wherein said second thread of said parallel processor is configured to correct said imaging signals based on a minimum variance mean-line subtraction (MVMS) method to at least partially remove said image artifacts, and
wherein said minimum variance mean-line subtraction (MVMS) method being implemented based on a recursion relation using:

$$\mu_{l+1}(z) = \mu_l(z) + \frac{1}{l+1}(g_l(z) - \mu_l(z)) \text{ and}$$

$$v(z)_{l+1}^2 = v(z)_l^2 + \frac{1}{l+1}\left[\frac{l}{l+1}(g_{l+1}(z) - \mu_l(z))^2 - v(z)_l^2\right]$$

where µ(z) is a mean value of said variance, l is a data point of a segment of A-line data, z is an axial position of the A-line data, g(z) is a complex A-line data point, and v(z) is a segmental variance.

2. An optical coherence tomography system according to claim 1, wherein said parallel processor comprises at least one graphics processing unit (GPU).

3. An optical coherence tomography system according to claim 1, wherein said optical coherence tomography system is configured to provide image rendering at at least ten (10) image frames per second in said third thread,
wherein each image frame has a size that is at least 512× 512 pixels, and
wherein each image frame is corrected in real time to at least partially remove image artifacts and saturation based on a subset of image data within each respective image frame.

4. An optical coherence tomography system according to claim 1, wherein said optical coherence tomography system is configured to provide image rendering at at least seventy (70) image frames per second in said third thread,
wherein each image frame has a size that is at least 1000× 1024 pixels, and
wherein each image frame is corrected in real time to at least partially remove image artifacts and saturation based on a subset of image data within each respective image frame.

5. An optical coherence tomography method, comprising:
receiving imaging signals from a Fourier Domain optical coherence tomography unit;
correcting said imaging signals, in real time, using a parallel processor to at least partially remove image artifacts and saturation based on a subset of image data within an image frame, said parallel processor being configured for multithreaded operation comprising a first thread for data acquisition of said imaging signals from said optical coherence tomography unit, a second thread for data processing of said imaging signals, and a third thread for image display of image frames generated from said second thread; and
displaying a multiframe video after said correcting in real time,
wherein said first, second, and third threads are synchronized such that said second thread is triggered by said first thread, and said third thread is triggered by said second thread,
wherein said correcting said imaging signals includes, in said second thread of said parallel processor, subtracting a reference A-line from said imaging signals, said reference A-line being represented by a data structure unit of three floating point numbers including a mean value of a real part of said imaging signals, a mean value of an imaginary part of said imaging signals, and a variance of said imaging signals,
wherein said second thread of said parallel processor is configured to detect saturation in an A-line of said image frame and to correct said A-line based on a non-saturated A-line within said image frame, said non-saturated A-line within said image frame being a nearest non-saturated A-line to said saturated A-line within said image frame,
wherein said second thread of said parallel processor is configured to correct said imaging signals based on a minimum variance mean-line subtraction (MVMS) method to at least partially remove said image artifacts, said minimum variance mean-line subtraction (MVMS) method being implemented based on a recursion relation as follows:

$$\mu_{l+1}(z) = \mu_l(z) + \frac{1}{l+1}(g_l(z) - \mu_l(z)) \text{ and}$$

$$v(z)_{l+1}^2 = v(z)_l^2 + \frac{1}{l+1}\left[\frac{l}{l+1}(g_{l+1}(z) - \mu_l(z))^2 - v(z)_l^2\right]$$

where $\mu(z)$ is a mean value of said variance, l is a data point of a segment of A-line data, z is an axial position of the A-line data, g(z) is a complex A-line data point, and v(z) is a segmental variance.

6. An optical coherence tomography method according to claim 5, wherein said parallel processor comprises at least one graphics processing unit (GPU).

7. A non-transitory computer readable medium comprising software, which software when executed by a computer comprising a parallel processor causes the computer to:
receive imaging signals from a Fourier Domain optical coherence tomography unit;
correct said imaging signals, in real time, using said parallel processor to at least partially remove image artifacts and saturation based on a subset of image data within an image frame, said parallel processor being configured for multithreaded operation comprising a first thread for data acquisition of said imaging signals from said optical coherence tomography unit, a second thread for data processing of said imaging signals, and a third thread for image display of image frames generated from said second thread; and
display a multiframe video image after said correcting in real time,
wherein said first, second, and third threads are synchronized such that said second thread is triggered by said first thread, and said third thread is triggered by said second thread,
wherein to correct said imaging signals includes, in said second thread of said parallel processor, subtracting a reference A-line from said imaging signals, said reference A-line being represented by a data structure unit of three floating point numbers including a mean value of a real part of said imaging signals, a mean value of an imaginary part of said imaging signals, and a variance of said imaging signals,
wherein said second thread of said parallel processor is configured to detect saturation in an A-line of said image frame and to correct said A-line based on a non-saturated A-line within said image frame, said non-saturated A-line within said image frame being a nearest non-saturated A-line to said saturated A-line within said image frame, and
wherein said second thread of said parallel processor is configured to correct said imaging signals based on a minimum variance mean-line subtraction (MVMS) method to at least partially remove said image artifacts, said minimum variance mean-line subtraction (MVMS) method is implemented based on a recursion relation as follows:

$$\mu_{l+1}(z) = \mu_l(z) + \frac{1}{l+1}(g_l(z) - \mu_l(z)) \text{ and}$$

$$v(z)_{l+1}^2 = v(z)_l^2 + \frac{1}{l+1}\left[\frac{l}{l+1}(g_{l+1}(z) - \mu_l(z))^2 - v(z)_l^2\right]$$

where $\mu(z)$ is a mean value of said variance, l is a data point of a segment of A-line data, z is an axial position of the A-line data, g(z) is a complex A-line data point, and v(z) is a segmental variance.

8. A non-transitory computer readable medium according to claim 7, wherein said parallel processor comprises at least one graphics processing unit (GPU).

* * * * *